US012390233B2

(12) United States Patent
Reece

(10) Patent No.: US 12,390,233 B2
(45) Date of Patent: Aug. 19, 2025

(54) DRILL GUIDE

(71) Applicant: NuVasive, Inc., San Diego, CA (US)

(72) Inventor: Ryan Reece, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 147 days.

(21) Appl. No.: 18/482,764

(22) Filed: Oct. 6, 2023

(65) Prior Publication Data

US 2024/0050109 A1   Feb. 15, 2024

Related U.S. Application Data

(63) Continuation of application No. PCT/US2022/023597, filed on Apr. 6, 2022.

(60) Provisional application No. 63/172,444, filed on Apr. 8, 2021.

(51) Int. Cl.
*A61B 17/17* (2006.01)
*A61B 17/00* (2006.01)

(52) U.S. Cl.
CPC .... *A61B 17/1757* (2013.01); *A61B 2017/00477* (2013.01)

(58) Field of Classification Search
CPC .................................................. A61B 17/1757
See application file for complete search history.

(56) References Cited

U.S. PATENT DOCUMENTS

| | | | |
|---|---|---|---|
| 9,877,786 B2* | 1/2018 | Zastrozna | A61B 17/1757 |
| 10,070,873 B2* | 9/2018 | Courtney, Jr. | A61B 17/1624 |
| 10,136,902 B2* | 11/2018 | Farris | A61B 17/1655 |
| 10,149,733 B2* | 12/2018 | McCarthy | A61B 90/06 |
| 2011/0251597 A1* | 10/2011 | Bharadwaj | A61B 17/1757 606/1 |
| 2012/0191094 A1 | 7/2012 | Alain et al. | |
| 2019/0183516 A1 | 6/2019 | Peterson et al. | |

FOREIGN PATENT DOCUMENTS

WO   2022/216777 A1   10/2022

OTHER PUBLICATIONS

International Search Report and Written Opinion for PCT/US2022/023597 issued Jun. 27, 2022, 15 pages.

\* cited by examiner

*Primary Examiner* — Christian A Sevilla

(57) ABSTRACT

Disclosed herein are drill guides with a mechanism for use with different drills and with error resistance.

19 Claims, 13 Drawing Sheets

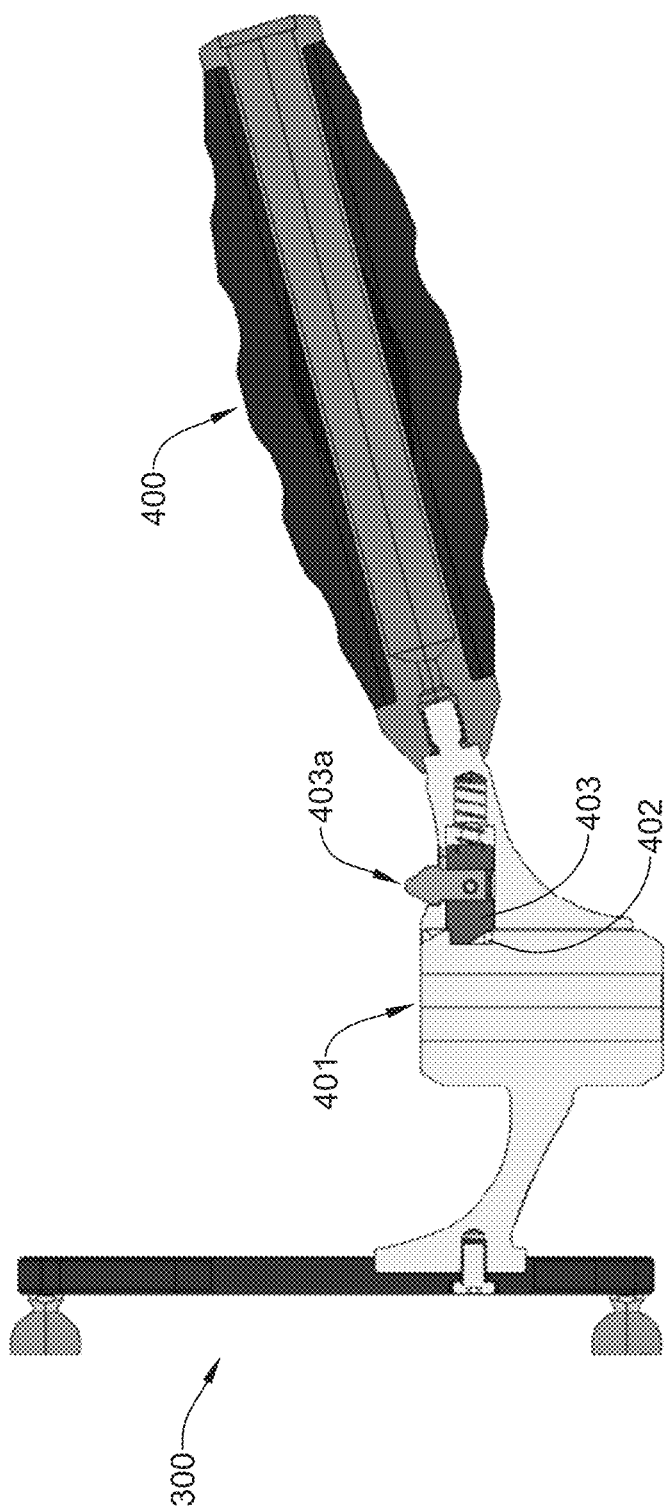

DRILL GUIDE

CROSS-REFERENCE TO RELATED APPLICATIONS

This application is a continuation of PCT Patent Application No. PCT/US2022/023597 filed Apr. 6, 2022, which claims priority to U.S. Provisional Application No. 63/172,444 filed Apr. 8, 2021, and titled DRILL GUIDE, which is hereby incorporated by reference in its entirety for any and all purposes.

BACKGROUND

The spine provides mobility, support, and balance. Spinal injuries can be debilitating, and even small irregularities in the spine can cause devastating pain and loss of coordination. Surgical procedures can be performed to treat the spine. To perform a surgical procedure on the spine, drill guides can be used to prepare for bone anchor insertion in an area of interest of the spine.

SUMMARY

Disclosures include surgical drill guides with an error resisting mechanism. The error resisting mechanism can be on a distal portion of drill guide and can allow easy manipulation by the user to securely engage different settings. Such settings can advantageously allow dynamic change of an internal diameter of the drill guide lumen. Such a drill guide can advantageously provide usage of and switching between different drill lengths and diameters (e.g., multiple different drill length and diameters). The error resisting mechanism can also advantageously resist a longer drill with larger diameter from being used when a shorter drill with a smaller diameter is selected to be used.

An example mechanism on a drill guide for insertion of different drills and error prevent includes an elongate body with a base and an outer sleeve, wherein the outer sleeve is rotatable and translatable with respect to the base to be in a first or second setting, an inner lumen within the elongate body, and an inner sleeve rotationally coupleable with the outer sleeve in the first or second setting thereby changing a diameter of the inner lumen, wherein, in the first setting, the inner lumen comprises a first diameter, and in the second setting, the inner lumen comprises a second diameter.

Alternatively or additionally to any of the embodiments in this section, base may comprise a proximal profile coupleable with a distal profile of the outer sleeve.

Alternatively or additionally to any of the embodiments in this section, one of the proximal profile and the distal profile comprises a groove, and the other of the proximal profile and the distal profile may comprise a tip that is coupleable to the groove in the first or second setting.

Alternatively or additionally to any of the embodiments in this section, one of the proximal profile and the distal profile comprises two groove separated by about 180 degrees, and the other of the proximal profile and the distal profile may comprise two tips separated by about 180 degrees, the two tips coupleable to the grooves in the first or second setting.

Alternatively or additionally to any of the embodiments in this section, the first setting corresponds to a first position of the outer sleeve and the second setting may correspond to a second position of the outer sleeve that is rotated at least 180 degrees relative to the first position.

Alternatively or additionally to any of the embodiments in this section, the outer sleeve may be translatable proximally relative to the base.

Alternatively or additionally to any of the embodiments in this section, the inner sleeve may comprise one or more channels in which one or more precision elements are configured to translate at least partly there through.

Alternatively or additionally to any of the embodiments in this section, the precision element comprises one or more precision balls.

Alternatively or additionally to any of the embodiments in this section, the one or more channels may start from an outer surface of the inner sleeve, and narrow to an inner surface of the inner sleeve.

Alternatively or additionally to any of the embodiments in this section, the one or more precision balls may be distributed evenly along a circumference of the inner sleeve.

Alternatively or additionally to any of the embodiments in this section, the one or more precision balls may comprise 3 precision balls separated by about 120 degrees.

Alternatively or additionally to any of the embodiments in this section, the outer sleeve may comprise one or more pockets in an inner surface thereof.

Alternatively or additionally to any of the embodiments in this section, in the first setting, the one or more pockets may be configured to hold at least a portion of the precision balls so that the one or more precision balls do not extend into the inner lumen.

Alternatively or additionally to any of the embodiments in this section, in the second setting, the one or more pockets may not be aligned with the one or more precision balls so that the one or more precision balls extend into the inner lumen.

Alternatively or additionally to any of the embodiments in this section, the first diameter is greater than the second diameter.

Alternatively or additionally to any of the embodiments in this section, the first diameter may be configured to allow passage of a first drill with a first drill depth, and the second diameter may be configured to allow passage of a second drill with a second drill depth.

Alternatively or additionally to any of the embodiments in this section, the first drill depth may be greater than the second drill depth.

Alternatively or additionally to any of the embodiments in this section, the outer sleeve may be rotatable relative to the inner sleeve.

Alternatively or additionally to any of the embodiments in this section, the outer sleeve may comprise one or more through windows, and the inner sleeve may comprise drill depth information configured to be visible from the one or more through windows.

Alternatively or additionally to any of the embodiments in this section, further including an energy biasing element configured to bias the outer sleeve distally toward the base.

Alternatively or additionally to any of the embodiments in this section, the mechanism may be configured to prevent error in using a first drill or a second drill.

Alternatively or additionally to any of the embodiments in this section, the mechanism may be configured to provide tactile, audio, or both feedback to a user when switching between the first setting and the second setting.

Alternatively or additionally to any of the embodiments in this section, the mechanism may be configured for an iliac drilling, thoracolumbar drilling, or both.

Alternatively or additionally to any of the embodiments in this section, the elongate body may be substantially cylindrical.

Alternatively or additionally to any of the embodiments in this section, at least part of the inner sleeve may be substantially cylindrical.

In another example, a drill guide with a mechanism for error prevention may include a mechanism on a proximal portion of the drill guide for inserting different drills and error prevention. The mechanism may include an elongate body with a base and an outer sleeve, wherein the outer sleeve is rotatable and translatable with respect to the base to be in a first or second setting, an inner lumen within the elongate body, and an inner sleeve rotationally coupleable with the outer sleeve in the first or second setting thereby changing a diameter of the inner lumen. In the first setting, the inner lumen comprises a first diameter, and in the second setting, the inner lumen may include a first drill with the first diameter and a first drill depth, a second drill with the second diameter and a second drill depth, wherein the first diameter is greater than the second diameter, and the first drill depth is greater than the second drill depth, a handle at the proximal end of the drill guide, the handle is coupleable to the first and second drill, a tracking array fixedly attached to the drill guide for surgical navigation of the drill guide, and a second handle removably coupled to the drill guide, wherein the second handle is couplable to the drill guide in a plurality of discrete positions.

In a further example, a method includes providing a drill guide, providing a mechanism, coupling the mechanism to the drill guide, modifying a lumen diameter of a inner lumen of the mechanism from a first diameter to a second diameter, providing a drill having an outer drill diameter smaller than the first diameter and larger than the second diameter, inserting the drill into the inner lumen, and drilling bone with the drill.

In a further example, a method includes providing a mechanism coupled to a drill guide, the mechanism having an elongate body with a base, an outer sleeve, an inner lumen within the elongate body, and an inner sleeve, changing a diameter within the inner lumen, wherein changing the diameter includes rotating the outer sleeve with respect to the base to transition the elongate body from a first setting corresponding to a first diameter to a second setting corresponding to a second diameter, and inserting a drill through the mechanism.

Alternatively or additionally to any of the embodiments in this section, rotating the outer sleeve with respect to the base may include causing a proximal profile to leave alignment with a first groove and enter alignment with a second groove.

Alternatively or additionally to any of the embodiments in this section, changing the diameter of the inner lumen further may include proximally translating the outer sleeve relative to the base.

Alternatively or additionally to any of the embodiments in this section, the rotating of the outer sleeve may modify an area in which one or more balls can travel, and the one or more balls at least in part may define the diameter within the inner lumen.

Alternatively or additionally to any of the embodiments in this section, the method may further include revealing a first drill depth indicia through a window of the outer sleeve, wherein changing the diameter within the inner lumen causes second drill depth indicia to be revealed through the window.

Alternatively or additionally to any of the embodiments in this section, the method may further include overcoming a bias force that urges the outer sleeve distally toward the base.

Alternatively or additionally to any of the embodiments in this section, the method may further include resisting an error in using an incorrect drill by changing the diameter.

Alternatively or additionally to any of the embodiments in this section, the method may further include performing one or both of iliac drilling and thoracolumbar drilling.

Alternatively or additionally to any of the embodiments in this section, the method may further include coupling the mechanism to the drill guide.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

FIG. 7B shows a cross section view of the removable handle in FIG. 7A.

DETAILED DESCRIPTION OF THE DISCLOSURE

Disclosed drill guides can include an error resisting mechanism that permits rotation of an outer sleeve of the mechanism to securely engage different settings, such as the diameter of an inner lumen. The mechanism can permit the use of different drill depths and diameters with a single drill guide. This mechanism can be useful in preventing a longer drill with larger diameter from being used when a shorter drill with a smaller diameter is selected to be used or needed. For example, drill bits having longer lengths may have larger diameters. The mechanism may permit a user to select a desired drill length by setting the diameter of the inner lumen. Such a step can prevent or resist the inadvertent use of a longer than desired drill.

Disclosed mechanisms can be compatible with traditional drill guides and can advantageously provide error prevention and insertion of different drills. The mechanism can include an outer sleeve that rotates between two or more discrete settings. For example, the rotation can be across a predetermined range (e.g., 180 degrees). The outer sleeve can have one or more windows to permit a user to see information, such as drill depth. The outer sleeve can have multiple pocket features. These pocket features can either align or not align with precision elements captured between the outer sleeve and an inner sleeve defining the inner lumen for passing drills therethrough. When the outer sleeve is aligned with a first setting (e.g., about 15 mm to about 45 mm) the pocket features do not align with the precision elements (e.g., precision balls), the outer sleeve can force the precision elements inward thereby reducing the internal diameter of the inner lumen. This reduction then will only allow about 15 mm to about 45 mm drill to pass through and be used. When the outer sleeve is pulled and rotated (e.g., for about 180 degrees), pockets align with the precision balls, allowing the precision balls to fall into these pockets thereby allowing the internal diameter of the drill guide to increase. The increased diameter then can allow about 60 mm to about 90 mm drill to be inserted. The mechanism can be integral with a drill guide or be attached to an existing drill guide. A drill guide can be configured for particular procedures, such as iliac procedures, thoracolumbar procedures, or both.

Figure 1:
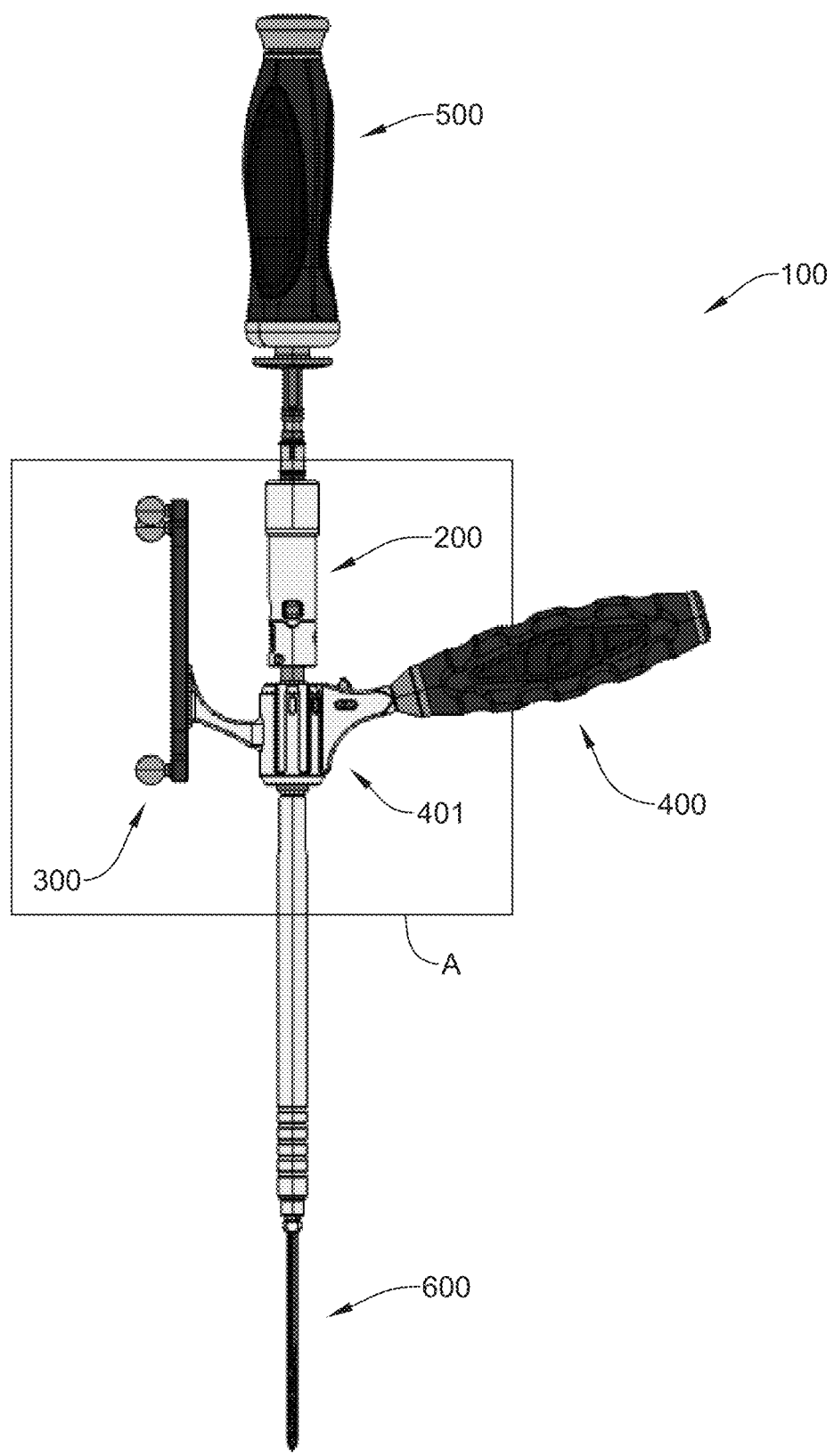
FIG. 1 shows a side view of an example drill guide with a mechanism for inserting different drills and error prevention.
Figure 2:
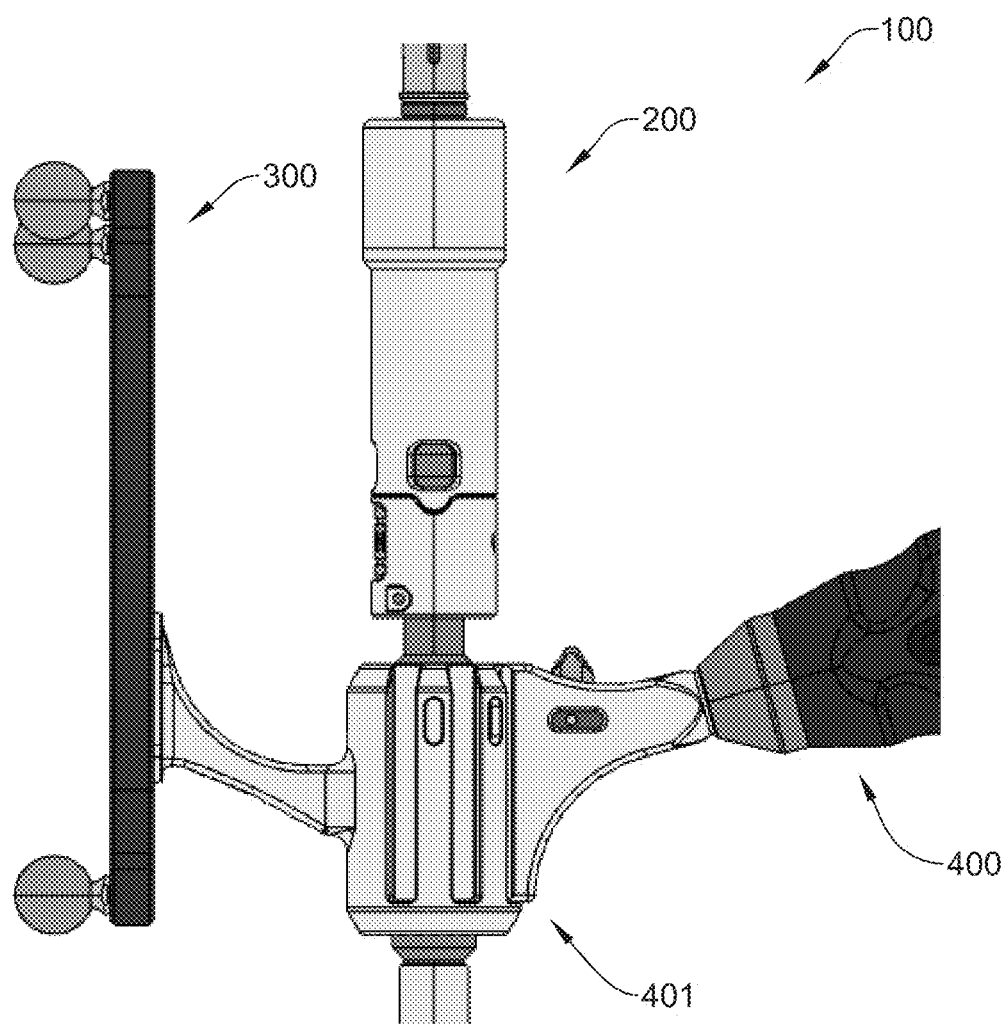
FIG. 2 shows an enlarged view of a portion of the drill guide depicted in box A of FIG. 1.

FIGS. 1 and 2 show an example implementation a drill guide 100. The drill guide 100 includes a mechanism 200 for inserting different drills and for error resistance. In the illustrated example, the mechanism 200 is part of the drill guide 100 and coupled with a connector 401 of the drill guide 100. The coupling can be achieved through any of a variety of mechanism, such as via user-releasable couplings (e.g., screw-fit or snap-fit mechanism) or unreleasable couplings (e.g., via one or more welds or integral bonds). The drill guide 100 can also include a tracking array 300 for surgical navigation, such as by including multiple active or passive fiducials. A handle 500 for inserting a drill 600 can also be included, such as by being inserted through the drill guide 100. Another removable handle 400 can also be fixedly attached to the drill guide 100 for facilitating control of the drill guide 100 without interference with the drill handle 500.

FIG. 2 shows an enlarged view of the contents of box-A in FIG. 1, which include at least portions of the mechanism 200, the tracking array 300, and the removable handle 400. Additional details regarding the mechanism 200 are provided in FIGS. 3A and 3B, below.

Figure 3A:
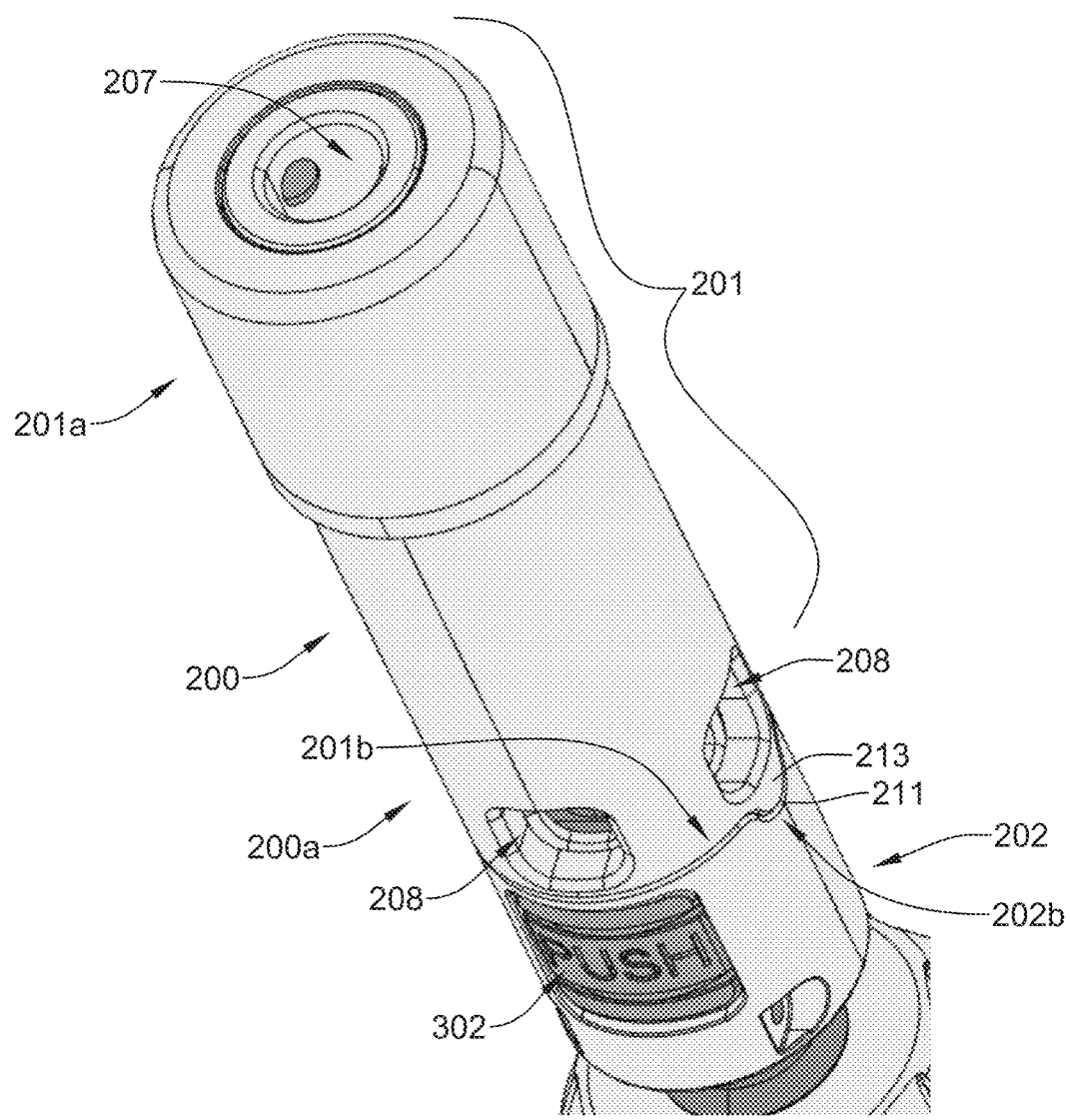
FIG. 3A shows a perspective view of the mechanism of the drill guide.
Figure 3B:
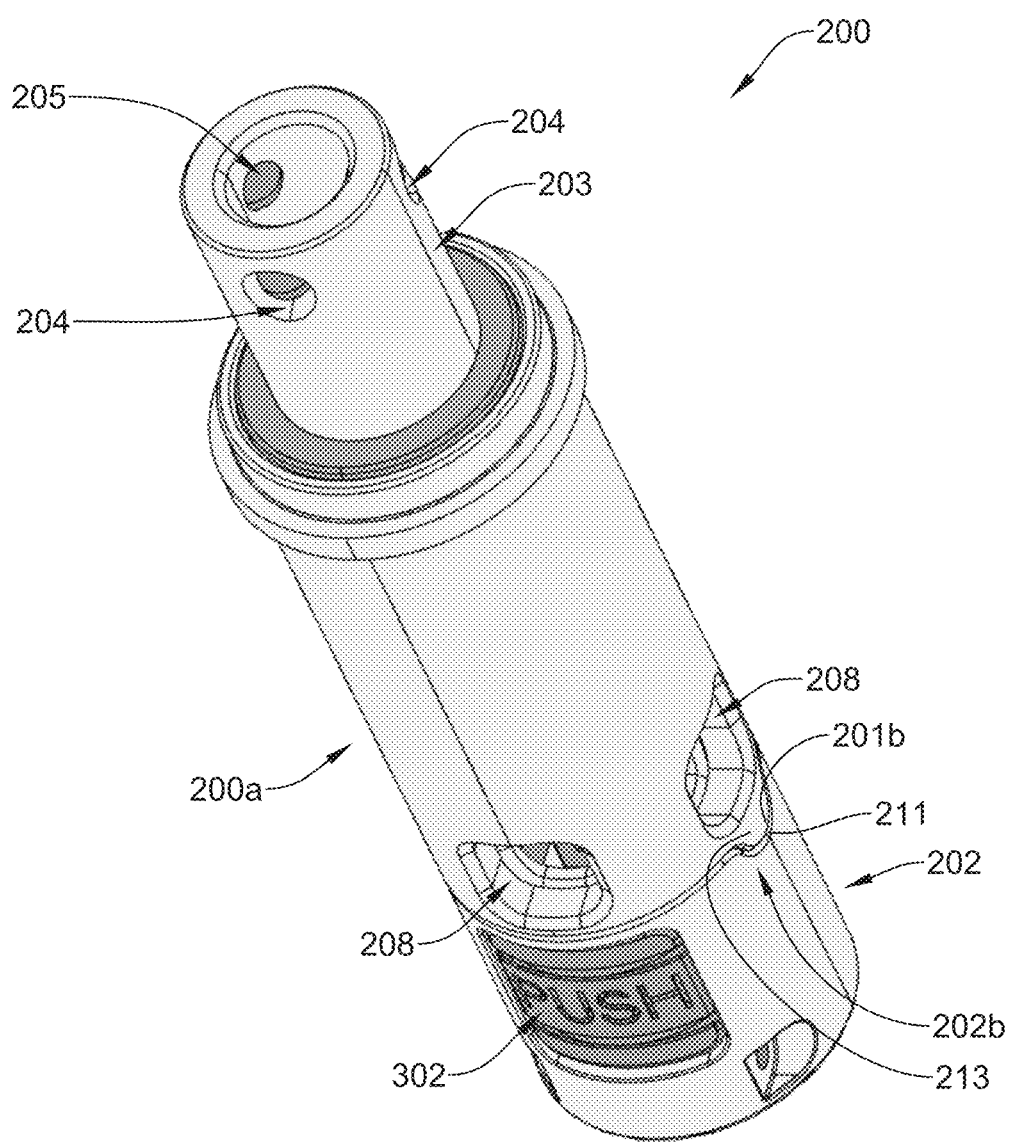
FIG. 3B shows a perspective view of the mechanism of the drill guide with a portion of an outer sleeve omitted.
Figure 4A:
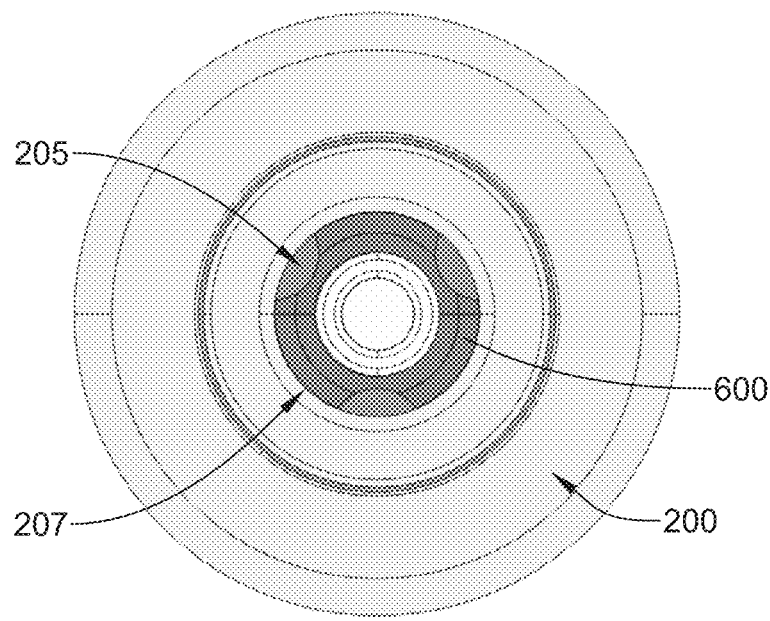
FIG. 4A shows a top view of the mechanism with a drill disposed in a lumen, where the drill is shown in cross-section at the top of the mechanism.
Figure 4B:
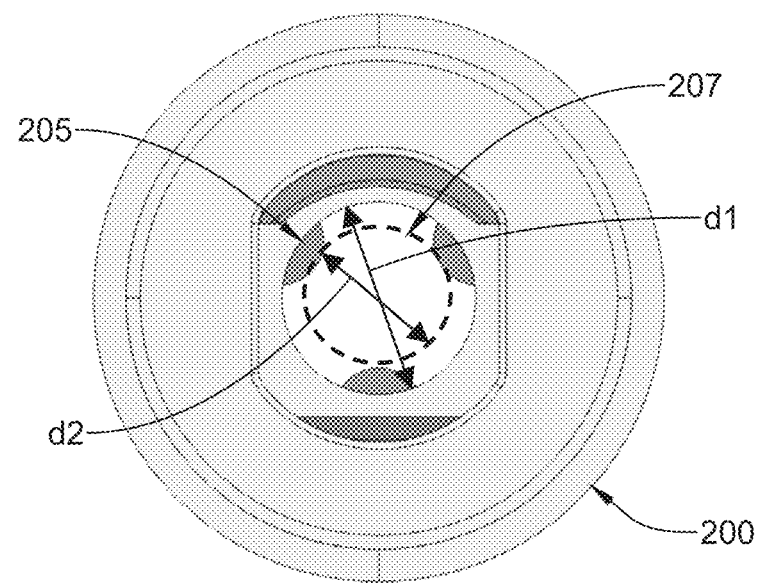
FIG. 4B shows a bottom view of the mechanism without the drill in the lumen.

FIGS. 3A and 3B show the mechanism 200 in perspective views, with and without a cap 201a of an outer sleeve 201, respectively. FIGS. 4A and 4B further show an inner lumen 207 of the mechanism 200.

The mechanism 200 includes an elongate body 200a that can be substantially cylindrical. Other geometric shapes can be used for the elongate body 200a. The elongate body 200a includes a base 202. The outer sleeve 201 of the mechanism 200 is disposed proximal to the base 202 and includes the cap 201a at a proximal portion of the outer sleeve 201. The cap 201a can be fixedly or releasably coupled to the rest of the outer sleeve 201. The outer sleeve 201 is rotatable (e.g., by a user or a robotic arm) with respect to the base 202, to allow the mechanism 200 to be selectively disposed in one of a plurality of different settings, such as a first setting or a second setting. The outer sleeve 201 can be rotatable in one or more directions. In some implementation, the outer sleeve 201 is translatable along a proximal-distal axis of the mechanism 200. The outer sleeve 201 can be translated proximally by a user when the user is transitioning between the first and second setting. In an example, the outer sleeve is 201 is blocked from substantially rotation until the outer sleeve 201 is first translated proximally.

Figure 5A:
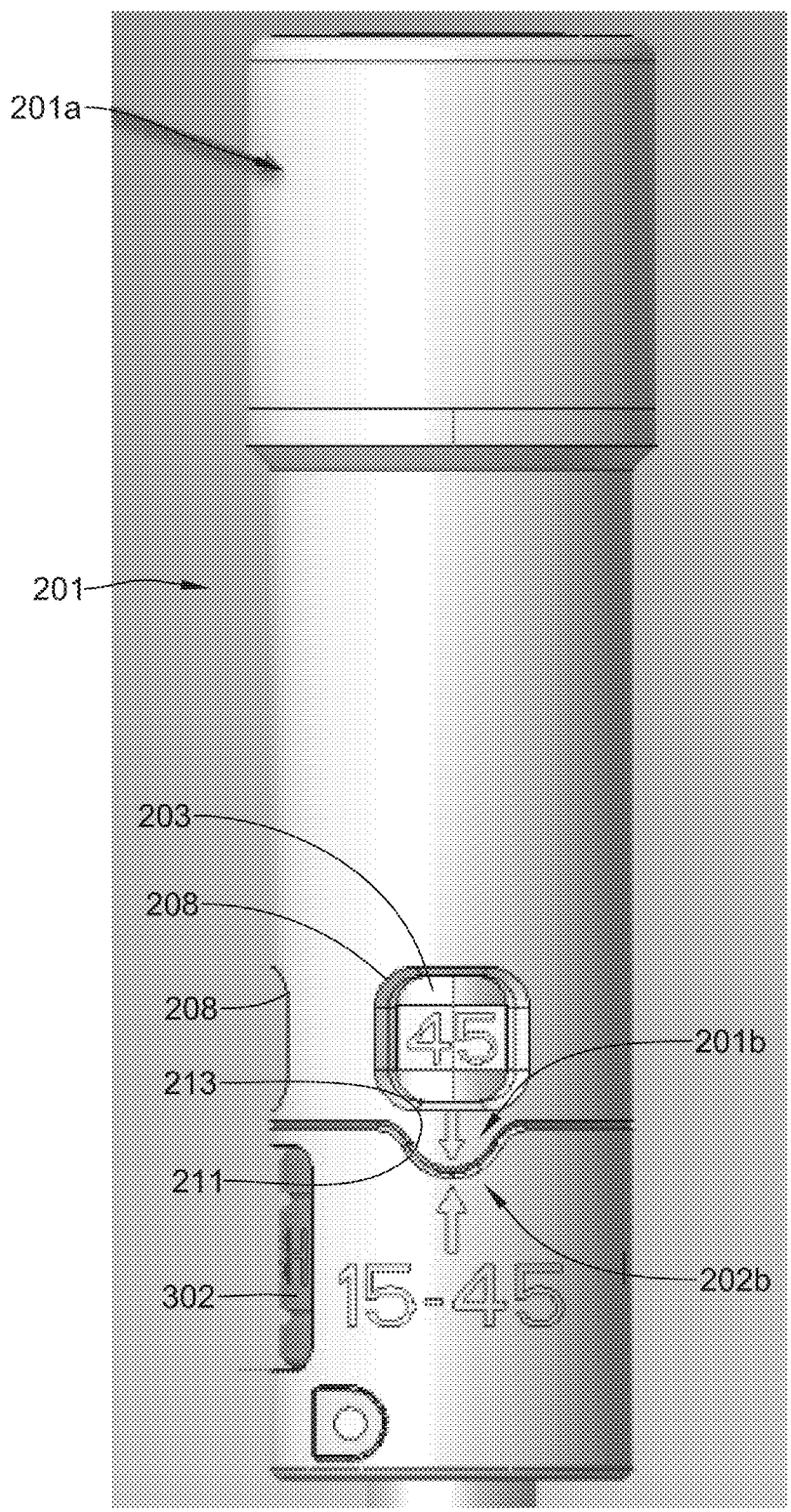
FIG. 5A shows a side view of the mechanism at a second setting.

The outer sleeve 201 can include a distal profile 201b at its distal end. The base 202 can include a proximal profile 202b at the proximal end of the base 202. The distal profile 201b and the proximal profile 202b can be a complementary geometric or other features configured to couple with each other when the mechanism is in a particular setting (e.g., the first or second setting as a result of being aligned in a particular manner). The distal profile 201b and the proximal profile 202b can be coupled with each other, in the first setting, and the second setting, respectively (e.g., as shown in more detail in FIGS. 5A and 5B). In the illustrated example, one of the proximal profile 202b and the distal profile 201b includes two grooves 211 (e.g., only one groove 211 is depicted at a time in the FIGS.) separated about 180 degrees, and the other of the proximal profile 202b and the distal profile 201b includes two matching tips 213 (e.g., only one tip 213 is depicted at a time in the FIGS.) coupleable with the two grooves 211. In other implementations, the proximal profile 202b and the distal profile 201b can take other forms, such as a ball-and-detent configuration. The distal profile 201b and the proximal profile 202b can disengage from each other when the mechanism is in none of the settings but in a transitioning stage. At the transitioning stage, the outer sleeve 201 can be translated proximally away from the base 202, with or without rotational movements relative to the base 202.

The mechanism 200 can include an inner sleeve 203 rotationally coupleable with the outer sleeve 201 in the settings (e.g., the first or second setting). The inner sleeve 203 can include one or more channels 204 in which one or more precision elements 205 are configured to translate at least partly therethrough.

The mechanism 200 can include an inner lumen 207 within the elongate body 200a, as shown in FIGS. 4A and 4B. The inner lumen 207 can allow a drill or other cylindrical tool to be inserted therethrough. The diameter of the inner lumen 207 can define the maximum size of the drill 600 that can fit therethrough.

In a first setting, the inner lumen 207 can have a first diameter d1 of the cross-section that is greater than a second diameter d2 in the second setting. The first diameter can allow passage of a first drill with a first drill depth, and the second diameter is configured to allow passage of a second drill with a second drill depth. The first drill depth can be greater than the second drill depth. When in the second setting, second diameter can resist the insertion of the first drill cannot be inserted into the drill guide, thereby preventing error of using a drill guide with a larger diameter and/or drill depth than needed.

Figure 5B:
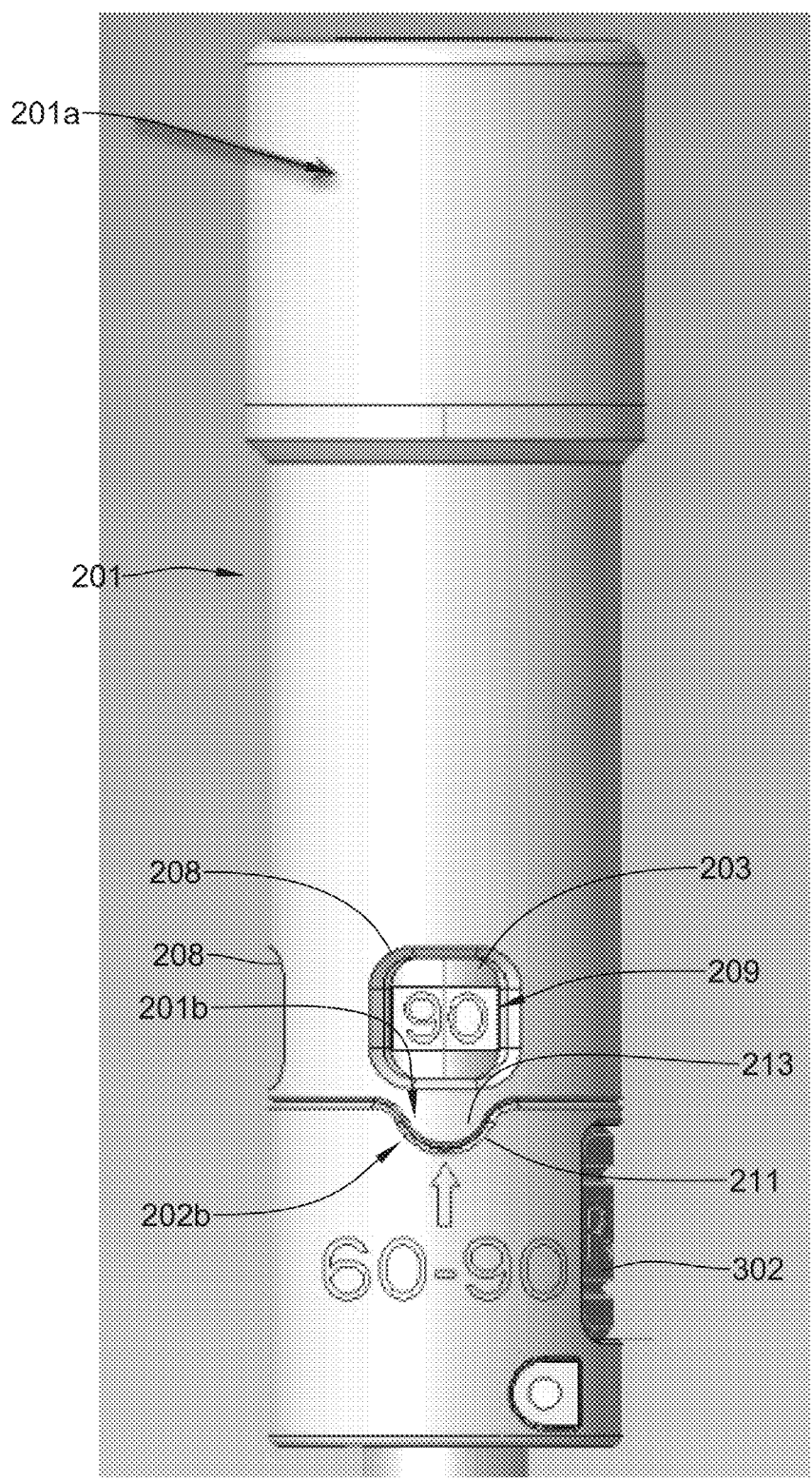
FIG. 5B shows a side view of the mechanism at a first setting.

The outer sleeve 201 can define one or more windows 208. The windows 208 can be areas through which the inner sleeve 203 is visible. The inner sleeve 203 can include drill depth or drill diameter information 209 configured to be visible from the window(s) 208. In the first setting, a user can see the drill depth or diameter information as shown in FIG. 5B, while in a second setting, a smaller drill depth or diameter information that is smaller can be seen through the window 208, as in FIG. 5A. Besides the visible drill depth or diameter information 209, the mechanism 200 may also provide tactile, audio, or both feedback to a user when the user is switching between the first and second settings.

The mechanism 200 may include an energy biasing element 210 (e.g., a spring) configured to bias the outer sleeve distally toward the base, especially when the user pulls the outer sleeve proximally to switch between settings, the energy biasing element 210 may facilitate the switching by biasing the outer sleeve 201 to couple distally to the base 202.

The mechanism 200 further includes an actuatable button 302. As shown in more detail in FIGS. 6A and 6B, the actuatable button 302 can be part of a mechanism to capture a portion of the drill 600 (e.g., a sleeve thereof). Actuation of the actuatable button 302 can permit release of the drill 600.

Figure 6A:
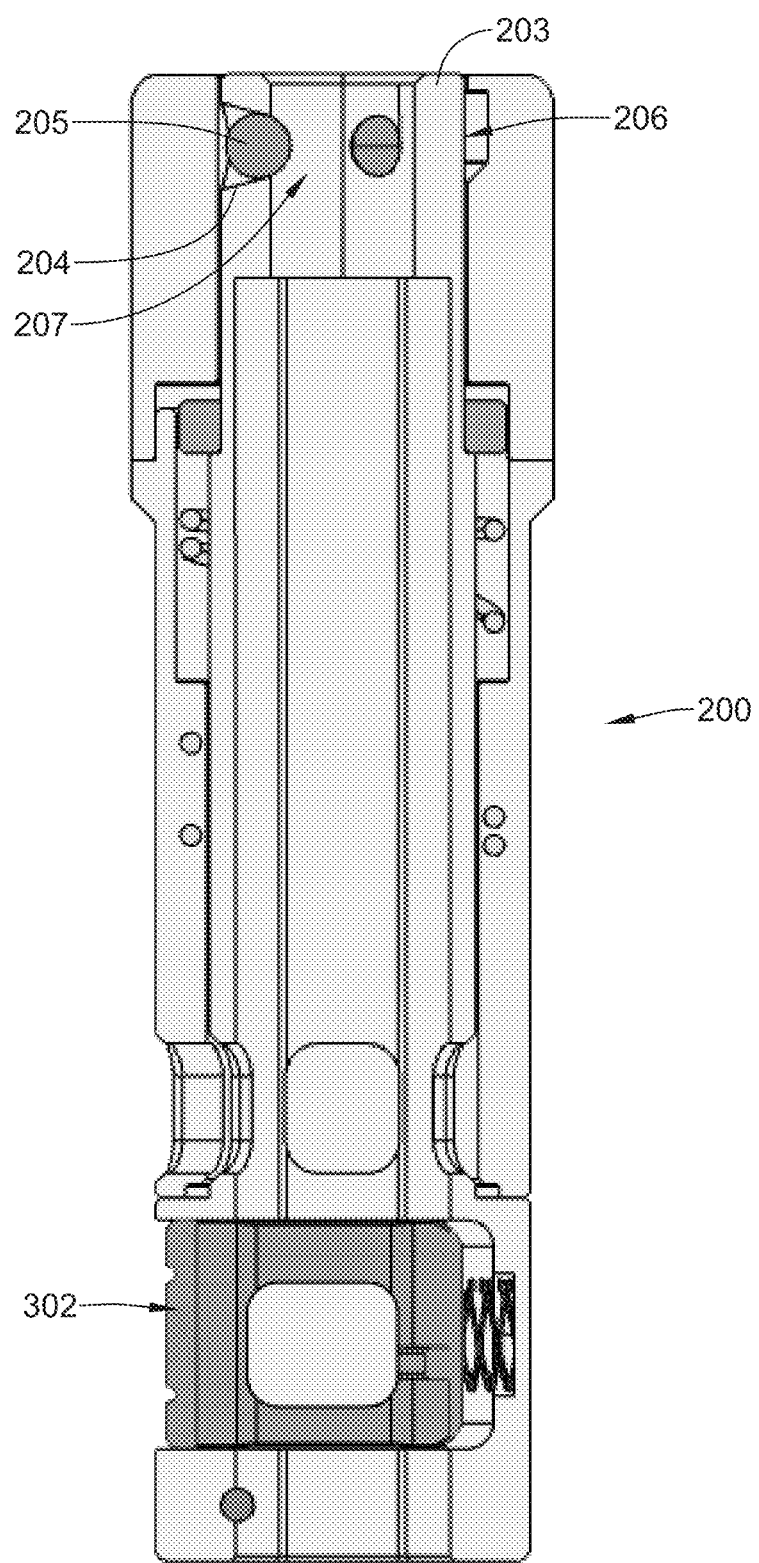
FIG. 6A shows a cross-section view of an example mechanism in the second setting without the drill inserted.
Figure 6B:
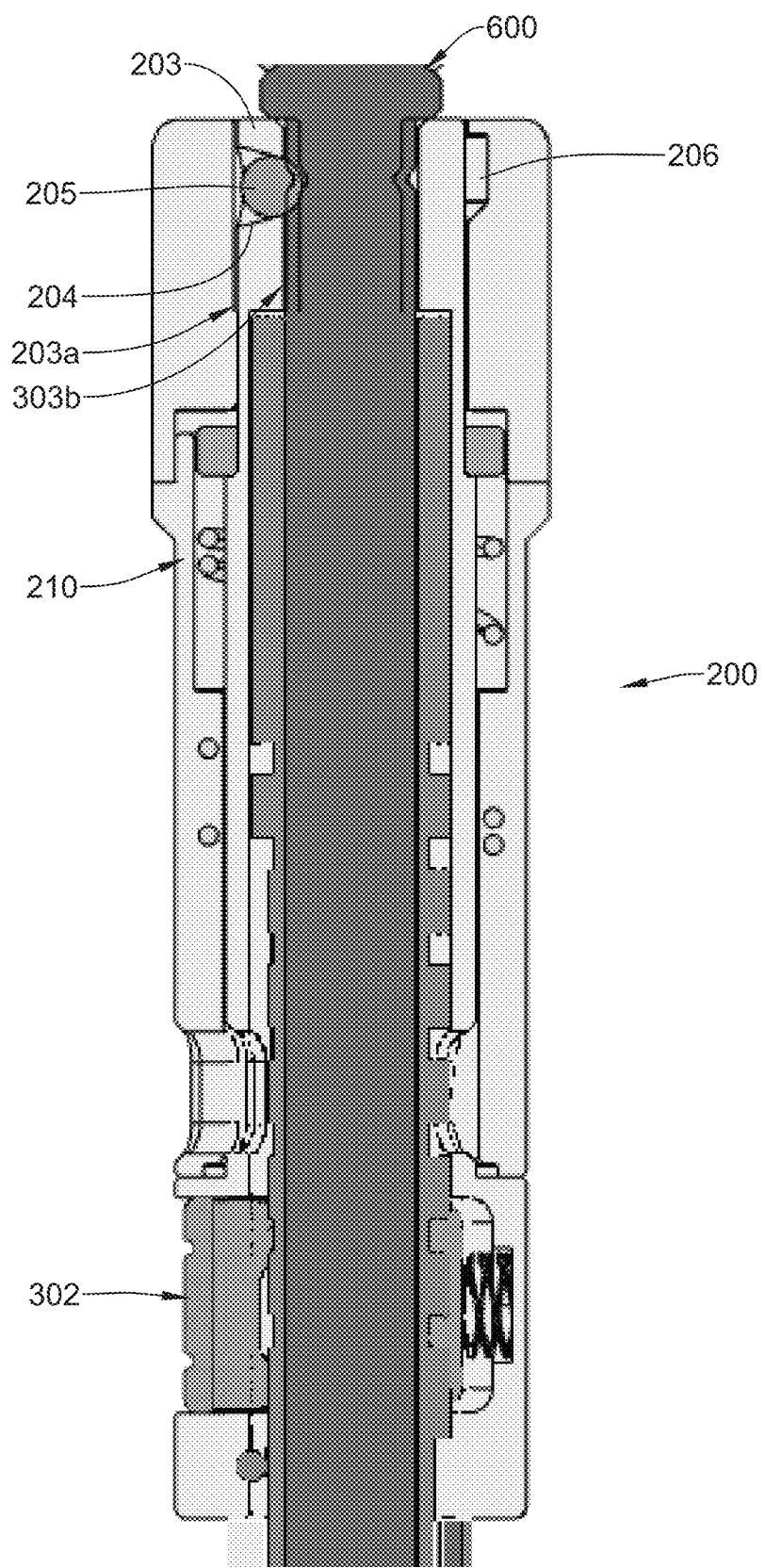
FIG. 6B shows a cross-section view of the example mechanism in the second setting with the drill inserted into the drill guide.
Figure 6C:
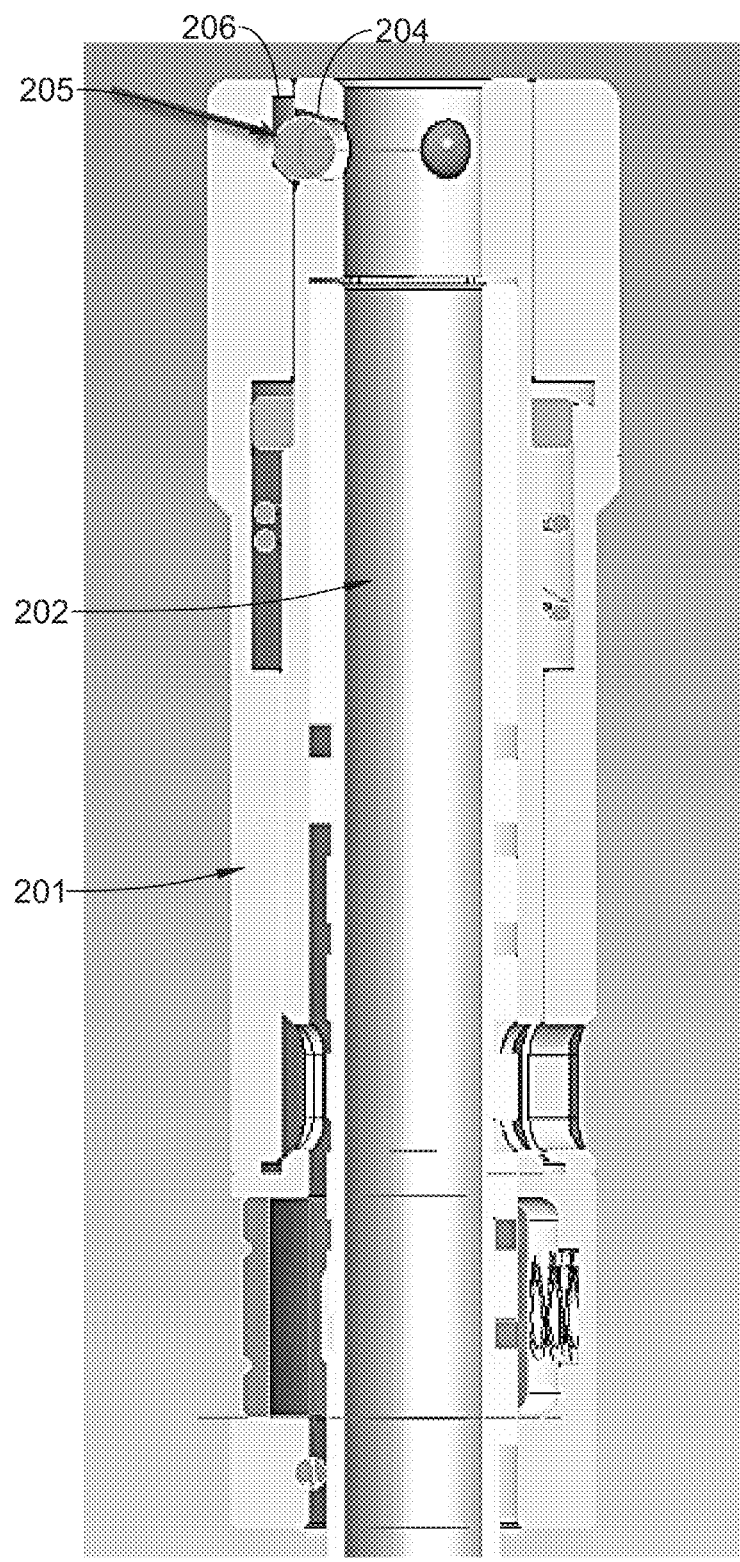
FIG. 6C shows a cross-section view of an example of the mechanism in the first setting.

FIGS. 6A-6C show cross-sectional views of the mechanism 200 at different settings. FIGS. 6A and 6B show the mechanism at the second setting, and FIG. 6C shows the mechanism at the first setting. As can be seen in FIG. 6B, one or more channels 204 can start from an outer surface 203a of the inner sleeve 203, and narrow to an inner surface 203b of the inner sleeve 203. The one or more channels 204 can be distributed evenly along a circumference of the inner sleeve 203. In this particular embodiment, three channels are separated evenly for about 120 degrees. The one or more precision elements 205 can also be distributed evenly along a circumference of the inner sleeve, as shown in FIGS. 4A-4B, separated for about 120 degrees. In this embodiment, the precision elements 205 are precision balls. In an example, the precision elements are "precision" in that they are precisely manufactured to meet tolerances for the application in which they are used. The outer sleeve 201 can have one or more pockets 206 in an inner surface thereof, and each pocket 206 can hold one precision element 205 therewithin when aligned, as shown in FIGS. 6A-6C. For example, the one or more pockets 206 can provide room for the precision elements 205 (e.g., precision balls, as depicted) to travel to permit an increase in the size of the diameter within the inner lumen 207. The mechanism 200 herein can include two or more different settings that a user may select from and conveniently transition between. In another example, the one or more pockets 206 can be in the form of steps or a ramp to provide different amounts of space to gradually or discontinuously provide diameter changes.

Referring to FIG. 6C, in the first setting, the one or more pockets 206 are configured to hold at least a portion of the one or more precision elements 205 so that the precision elements 205 do not extend inward into the inner lumen 207. The channels 204 can include a slope to facilitate the precision element 205 falling into the pocket 206 when the pocket 206 and the precision element 205 are aligned. In the second setting, when the outer sleeve 201 is rotated for about 180 degrees, as shown in FIGS. 6A and 6B, the one or more pockets 206, after the rotation, are not aligned with any of the precision elements 205 so that the precision elements 205 extend into the inner lumen 207. FIGS. 6A and 6B show the mechanism 200 at the first setting with and without the drill 600 inserted.

Figure 7A:
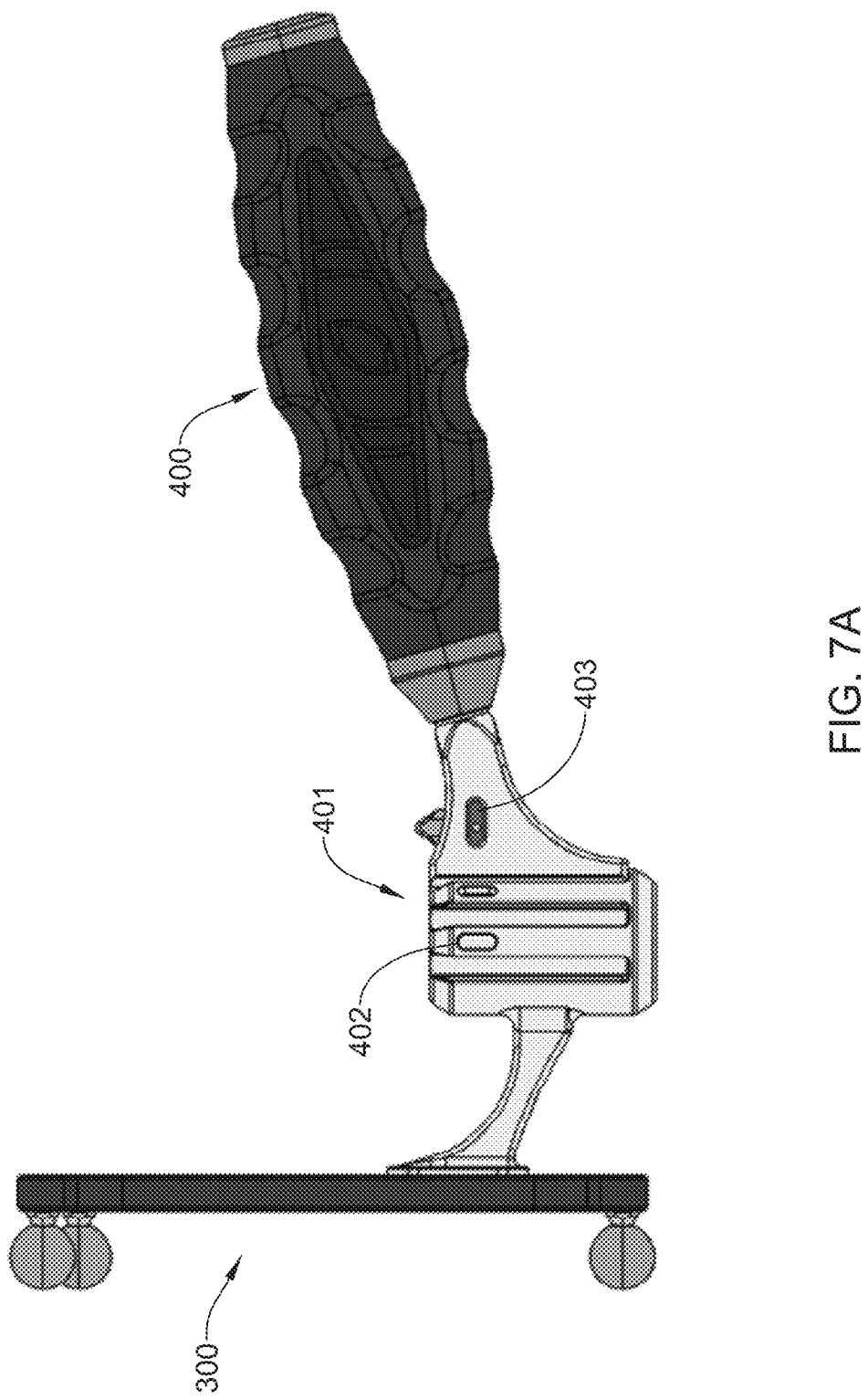
FIG. 7A shows a side view of the tracking array and the removable handle of the drill guide herein.

FIGS. 7A and 7B show an example removable handle 400 usable with the mechanism 200 (not depicted in FIGS. 7A and 7B), where FIG. 7A depicts a side view of the example removable handle 400 and FIG. 7B depicts a cross-sectional view of the example removable handle 400. The handle 400 may be coupled to the mechanism 200 via a connector 401. The connector 401 can be fixedly or adjustably coupled to the mechanism 200. The same connector 401 may enable the tracking array 300 to be fixedly attached thereon. The handle 400 may extend in a direction that is not along the proximal to distal direction. The handle 400 may have a fixed tilt angle from the proximal to distal direction. The connector 401 can include multiple coupling elements 402 that allow a user to attach the handle 400 to the drill guide 100. The handle can include a matching element 403 that can removably and fixedly attach to the coupling element 402. The coupling can be locked or unlocked using a quick release switch 403a. The connector 401 and handle 400 advantageously allow a user to couple the handle at one of the many discrete positions provided by the coupling elements 402 to maximize operational convenience and efficiency of the drill guide 100.

Figure 8:
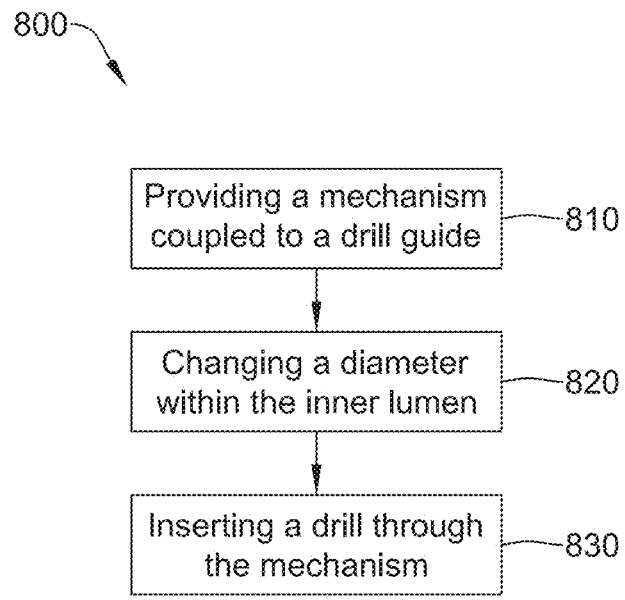
FIG. 8 illustrates a method.

FIG. 8 illustrates an example method 800 that includes operation 810, operation 820, and operation 830.

Operation 810 includes providing a mechanism 200 coupled to a drill guide 100. The mechanism 200 having an elongate body with a base 202, an outer sleeve 201, an inner lumen 207 within the elongate body, and an inner sleeve 203. In some examples, the mechanism 200 and drill guide 100 are integral. In some implementations, the method 800 can further include coupling the mechanism 200 to the drill guide 100, such as using a threaded or snap connector.

Operation 820 includes changing a diameter within the inner lumen 207. The operation 820 can include rotating the outer sleeve 201 with respect to the base 202 to transition the elongate body from a first setting corresponding to a first diameter to a second setting corresponding a second diameter. Rotating the outer sleeve 201 with respect to the base 202 can include causing a proximal profile 202b to leave alignment with a first groove and enter alignment with a second groove. The rotating of the outer sleeve 201 modifies an area in which one or more balls can travel, with the one or more balls at least in part define the diameter within the inner lumen. The operation 820 can include changing the diameter of the inner lumen 207 further includes proximally translating the outer sleeve 201 is relative to the base 202.

Operation 830 includes inserting a drill 600 through the mechanism 200.

In some examples, the method 800 further includes revealing a first drill depth indicia through a window 208 of the outer sleeve 201 and changing the diameter within the inner lumen 207 causes second drill depth indicia to be revealed through the window 208. The method 800 can further include overcoming a bias force that urges the outer sleeve 201 distally toward the base 202. The method 800 can include or result in resisting an error in using an incorrect drill by changing the diameter. The method 800 can include performing one or both of iliac drilling and thoracolumbar drilling while the drill 600 is inserted through the mechanism 200.

As disclosed herein, "proximal" indicates the direction away from attachment of an element to the subject, while "distal" indicates the direction opposite proximal direction and toward attachment of an element to the subject.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A mechanism on a drill guide for insertion of different drills and error prevention, the mechanism comprising:
   an elongate body with a base and an outer sleeve, wherein the outer sleeve is rotatable and translatable with respect to the base to be in a first or second setting;
   an inner lumen within the elongate body; and
   an inner sleeve rotationally coupleable with the outer sleeve in the first or second setting thereby changing a diameter of the inner lumen,
   wherein, in the first setting, the inner lumen comprises a first diameter, and in the second setting, the inner lumen comprises a second diameter;
   wherein the outer sleeve comprises a window and the inner sleeve comprises first and second indicia;
   wherein the first indicia can be revealed in the window; and
   wherein changing the diameter within the inner lumen causes the second indicia to be revealed through the window.

2. The mechanism of claim 1, wherein the base comprises a proximal profile coupleable with a distal profile of the outer sleeve.

3. The mechanism of claim 2, wherein one of the proximal profile and the distal profile comprises a groove, and the other of the proximal profile and the distal profile comprises a tip that is coupleable to the groove in the first or second setting.

4. The mechanism of claim 2, wherein one of the proximal profile and the distal profile comprises two grooves separated by about 180 degrees, and the other of the proximal profile and the distal profile comprises two tips separated by about 180 degrees, the two tips coupleable to the grooves in the first or second setting.

5. The mechanism of claim 1, wherein the first setting corresponds to a first position of the outer sleeve and the second setting corresponds to a second position of the outer sleeve that is rotated at least 180 degrees relative to the first position.

6. The mechanism of claim 1, wherein the outer sleeve is translatable proximally relative to the base.

7. The mechanism of claim 1, wherein the inner sleeve comprises one or more channels in which one or more precision elements are configured to translate at least partly there through.

8. The mechanism of claim 7, wherein the one or more precision elements comprises one or more precision balls.

9. The mechanism of claim 7, wherein the one or more channels start from an outer surface of the inner sleeve, and narrow to an inner surface of the inner sleeve.

10. The mechanism of claim 8, wherein the one or more precision balls are distributed evenly along a circumference of the inner sleeve.

11. The mechanism of claim 8, wherein the one or more precision balls comprises 3 precision balls separated by about 120 degrees.

12. The mechanism of claim 8, wherein the outer sleeve comprises one or more pockets in an inner surface thereof.

13. The mechanism of claim 12, wherein, in the first setting, the one or more pockets are configured to hold at least a portion of the precision balls so that the one or more precision balls do not extend into the inner lumen.

14. The mechanism of claim 12, wherein, in the second setting, the one or more pockets are not aligned with the one or more precision balls so that the one or more precision balls extend into the inner lumen.

15. A method comprising:
   providing a drill guide;
   providing a mechanism;
   coupling the mechanism to the drill guide;
   modifying a lumen diameter of an inner lumen of the mechanism from a first diameter to a second diameter;
   providing a drill having an outer drill diameter smaller than the first diameter and larger than the second diameter;
   inserting the drill into the inner lumen;
   revealing a first indicia through a window of an outer sleeve,
   wherein changing the diameter within the inner lumen causes second indicia to be revealed through the window; and
   drilling bone with the drill.

16. A method comprising:
   providing a mechanism coupled to a drill guide, the mechanism having an elongate body with a base, an outer sleeve, an inner lumen within the elongate body, and an inner sleeve;
   changing a diameter within the inner lumen, wherein changing the diameter includes rotating the outer sleeve with respect to the base to transition the elongate body from a first setting corresponding to a first diameter to a second setting corresponding to a second diameter; and
   inserting a drill through the mechanism;
   revealing a first indicia through a window of the outer sleeve,
   wherein changing the diameter within the inner lumen causes second indicia to be revealed through the window.

17. The method of claim 16, wherein rotating the outer sleeve with respect to the base includes:
   causing a proximal profile to leave alignment with a first groove and enter alignment with a second groove.

18. The method of claim 16, wherein changing the diameter of the inner lumen further includes:
   proximally translating the outer sleeve relative to the base.

19. The method of claim 16,
   wherein the rotating of the outer sleeve modifies an area in which one or more balls can travel; and
   wherein the one or more balls at least in part define the diameter within the inner lumen.

* * * * *